United States Patent [19]

Máthe et al.

[11] 4,361,500
[45] Nov. 30, 1982

[54] PROCESS FOR THE PREPARATION OF SUPPORTED METAL CATALYSTS

[75] Inventors: Tibor Máthe; Antal Tungler; Jozsef Petró, all of, Budapest, Hungary

[73] Assignee: Magyar Tudomanyos Akademia Kosponti Hivatala, Budapest, Hungary

[21] Appl. No.: 264,802

[22] Filed: May 18, 1981

Related U.S. Application Data

[63] Continuation-in-part of Ser. No. 150,077, May 15, 1980, abandoned.

[30] Foreign Application Priority Data

May 22, 1979 [HU] Hungary .............................. MA 3151

[51] Int. Cl.$^3$ ........................ B01J 31/28; B01J 31/26; B01J 37/02; B01J 21/18
[52] U.S. Cl. .................................... 252/430; 252/447; 252/456; 252/457; 252/460; 252/466 PT; 252/472; 252/473; 252/475; 252/476; 260/690
[58] Field of Search ............ 252/447, 444, 460, 466 B, 252/466 PT, 472, 476, 430

[56] References Cited

U.S. PATENT DOCUMENTS

| | | | |
|---|---|---|---|
| 2,760,940 | 8/1956 | Schwarzenbek | 252/466 PT |
| 2,852,474 | 9/1958 | Arnmdale et al. | 252/466 PT |
| 3,600,330 | 8/1971 | Schneble, Jr. et al. | 252/430 |
| 4,239,653 | 12/1980 | Bodnar et al. | 252/447 |

FOREIGN PATENT DOCUMENTS 1510195 5/1978 United Kingdom ................ 252/447

Primary Examiner—P. E. Konopka

[57] ABSTRACT

The invention relates to a new process for the preparation of a supported metal catalyst containing at least one metal belonging to Group A and optionally at least one metal belonging to Group B, wherein Group A encompasses the metals palladium, rhodium, ruthenium, platinum, iridium, osmium, silver, gold and cadmium and Group B encompasses the metals zinc, mercury, germanium, tin, antimony and lead. According to the invention, the metal(s) is (are) applied onto the support in the presence of at least one compound of the general formula (I),

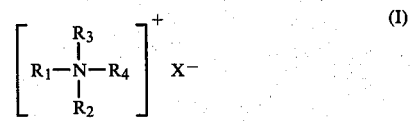

wherein
$R_1$, $R_2$, $R_3$ and $R_4$ each stands for a straight-chained or branched $C_{1-20}$ alkyl group, a $C_{1-4}$ hydroxyalkyl group or a phenyl-($C_{1-4}$ alkyl) group optionally having additional substituents, preferably $C_{1-4}$ alkyl groups, on the phenyl ring, and
X is hydroxy group or the residue of an organic or mineral acid.

According to the invention, highly active catalysts can be prepared by an easy and economical process.

10 Claims, No Drawings

PROCESS FOR THE PREPARATION OF SUPPORTED METAL CATALYSTS

RELATED APPLICATION

This application is a continuation-in-part of application Ser. No. 150,077 filed May 15, 1980, and now abandoned.

The invention relates to a new method for the preparation of supported metal catalysts. According to the method of the invention, certain of the known catalytically active metals and mixtures thereof can be applied on materials commonly used as supports for catalysts.

The invention also relates to supported metal catalysts prepared by the new method.

Several processes have been developed so far, particularly in the last decade, for the preparation of supported metal catalysts. All these methods aim at distributing the catalytically active metal on the support as finely as possible. Fine distribution of the catalytically active metal is essential, since the finer the distribution of the catalytically active metal (i.e., the greater the share of the surface metal atoms in the total number of metal atoms applied), the more the metal applied participates in the catalytic reaction. In a large number of reactions, the increase in dispersibility involves an increase in catalytic activity. This means that a significantly higher amount of the starting substance can be converted into the desired end-product with a unit weight of catalytically active metal, which also means considerable economical advantages, particularly for the rather expensive noble metal catalysts.

Supported catalysts which contain the metal in relatively fine distribution can be prepared, e.g., according to the method described in the published printed Dutch patent application Nos. 67/5,259 and 68/13,236, so that the metal is precipitated onto the surface of the support as an insoluble salt or hydroxide under carefully controlled conditions. Thus, e.g., silicon dioxide of high surface area (Aerosil) is suspended in nickel nitrate solution, and nickel is deposited onto the surface of the support as a hydroxide by adding urea or another basic substance to the mixture. The support covered with nickel hydroxide is then calcined in air at 350° C., and reduced in a hydrogen stream at high temperatures (350° to 550° C.).

The method described by Hathaway and Lewis (J. Chem. Soc. A 6194 (1969)) resembles in some respects the above process. According to this method, the silicon dioxide support of high surface area (Aerosil) is subjected to cation exchange with sodium ions, and then the support is suspended in a solution prepared by admixing nickel nitrate solution with a calculated amount of ethylene diamine. The suspension is stirred for a pre-determined period, and then the solid is filtered off, washed and dried. Thereafter, as in the method discussed above, the solid is calcined and reduced with hydrogen at high temperatures.

Morkiawa, K., Shirasaki, T. and Okada, M. described a method for producing nickel and palladium catalysts on an alumino-silicate support in a comprehensive paper (Advances in Catalysis, p. 113, 1969). Aluminum silicate, calcined at 500°–750° C., is stored in 0.1 N aqueous ammonium hydroxide solution for one week to effect cation exchange with ammonium ions; thereafter the support is filtered off, dried, added to an aqueous solution of nickel nitrate or palladium chloride, and the suspension is allowed to stand for one week. After this period, the solid is filtered off, dried, and reduced in a hydrogen stream at 550° C. for nickel or at 300° C. for palladium.

The method elaborated originally by Zhmud et al. (Zhmud, E. S., Boronin, V. S., Poltorak, O. M.: Zhurn. Phys. Khim. 39.431 (1965)) is applied relatively widely for the preparation of finely distributed noble metal catalysts. In this process, a support which contains terminal groups capable of ion exchange, particularly silicon dioxide with high surface area (Aerosil), is treated with a solution of a noble metal-tetramine complex at a controlled pH value. The complex solution is prepared by adding an excess of ammonium hydroxide to a salt of the noble metal. Ion exchange proceeds between the complex cation (such as Pd $(NH_3)_4^{2+}$) and the terminal groups of the support so that the noble metal is bound on the surface of the support as a complex ion. The ion-exchanged support is washed, dried, and then heated to 300° C. at a controlled rate in a nitrogen stream. After the decomposition of the tetramine complex (which requires about 1 to 4 hours of heat treatment), a small amount of hydrogen is introduced into the nitrogen stream, and then the ratio of hydrogen is gradually increased, thereby reducing the catalyst. The distribution of the metal on the surface and its dispersibility greatly depend on the conditions of ion exchange, drying, heat treatment and reduction. Several publications deal with the effects of these factors.

U.S. Pat. No. 2,852,474, to Arundale et al., teaches that a catalyst can be dried more quickly and at a higher temperature if the catalytically active metal is deposited onto a support in the presence of a wetting and/or dispersing agent. Quaternary ammonium compounds are listed as suitable wetting agents. However, the patentees did not recognize that said wetting agents could influence the properties of the catalysts to be prepared. They could not recognize this because they carried out the drying of the catalysts at 800° to 1000° F., i.e., at temperatures higher than 420° C. At such high temperatures, the quaternary ammonium compounds are totally decomposed. This is established by the fact that the patentees called these materials "non-ashing" components. (e.g., at column 3, lines 18–19).

British Pat. No. 1,510,195 relates to the preparation of selective hydrogenation catalysts. These catalysts are prepared in a traditional manner by using polyvinyl alcohol as dispersing agent. The latter is removed from the catalysts of this patent by aqueous washing. Thus, the dispersing agent cannot influence the properties of the resulting catalysts.

According to U.S. Pat. No. 2,760,940, to Schwarzenbek, noble metal catalysts are prepared from metal complexes formed with ammonia or amines. Said complexes are calcined at a temperature of at least 600° F. (316° C.) prior to depositing the metal by reduction.

A common disadvantage of the known methods is that they are rather sophisticated, time-consuming, multistep procedures, and the parameters of the individual steps must be set very accurately to obtain a catalyst of the required quality. Thus, it is fairly difficult to produce catalysts with uniform quality characteristics, and the costs of production are undesirably high. In the majority of the known processes, the support has to be subjected to a specific pre-treatment, and almost exclusively silicon dioxide can be applied as the support. A further disadvantage is that only a small number of catalytically active metals (e.g., only nickel or only metals of the platinum group) can be applied onto the support by these known methods. Moreover, the catalysts prepared by the known methods exert satisfactory activity in hydrogenation reactions generally only at temperatures above 100° C.

The present invention provides a simple process which enables one to apply certain of the known catalytically active metals in highly disperse and highly active form onto the surface of materials commonly applied as catalyst supports.

The invention is based on the finding that supported catalysts containing the catalytically active metal(s) in highly disperse and highly active form can be prepared by applying the metal(s) in question onto the support in the presence of at least one compound of the general formula (I),

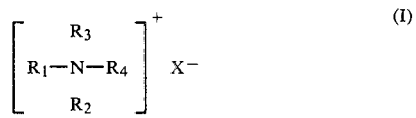

wherein $R_1$, $R_2$, $R_3$ and $R_4$ each stands for a straight-chained or branched.

$C_{1-20}$ alkyl group, a $C_{1-4}$ hydroxyalkyl group or a phenyl-($C_{1-4}$ alkyl) group optionally having additional substituents, preferably $C_{1-4}$ alkyl groups, on the phenyl ring, and X is hydroxy group or the residue of an organic or mineral acid.

In other respects, the catalysts are prepared by conventional methods, i.e., the metals are deposited by reduction, or the support is impregnated with a solution containing the ions or compounds of the metal(s) in question, and then the solid is reduced. Such reduction is effected at a temperature not exceeding 300° C., mostly at ambient temperature. Further, there is no calcining step.

It has been observed further that the dispersibility of the catalytically active metal on the surface of the support can be varied within wide limits by the proper selection of the nature of the substituents $R_1$, $R_2$, $R_3$ and $R_4$ in the compounds of the general formula (I). It was also found that more than one metal, i.e., two or more catalytically active metals or a catalytically active metal and a metal generally regarded as inactive in catalytic processes or catalytically inactive under certain conditions, can be applied together onto the surface of the support by the method of the invention. Catalysts applicable in stereospecific or enantioselective hydrogenation can also be prepared by the method of the invention, utilizing optically active compounds of the general formula (I), i.e., compounds in which one of the substituents contains a chiral carbon atom. On the basis of the above findings, the activity and selectivity of the catalysts prepared according to the invention can be varied over a wide range.

The catalytically active metals applicable on the surface of the support by the method of the invention are as follows: palladium, rhodium, ruthenium, platinum, iridium, osmium, silver, gold and cadmium (further on: metals belonging to Group A). Beside these catalytically active metals, inactive metals, i.e. zinc, mercury, germanium, tin, antimony and lead (further on: metals belonging to Group B), can also be applied on the support.

Any of the known substances commonly used as supports for catalysts can be used as a support in the method of the invention. Of the most important supports, the following are to be mentioned; activated carbons of various grades, aluminum oxides, silicon dioxides, aluminosilicates and various molecular sieves. It is particularly preferred to apply activated carbon and certain molecular sieves as supports; in some instances, however, relatively less frequently applied supports, such as barium sulfate, etc., can also be utilized to advantage.

Substituents $R_1$, $R_2$, $R_3$ and $R_4$ of the quaternary ammonium compounds having the general formula (I) may be the same or different, and may represent, e.g., methyl, ethyl, propyl, butyl, isobutyl, octyl, hexadecyl (in general: straight-chained or branched alkyl), furthermore benzyl, methylbenzyl and hydroxyethyl groups. Anion $X^-$ of the quaternary ammonium compounds having the general formula (I) may be hydroxy ion or an anion derived from a mineral or organic acid, of which the following are to be mentioned: $Cl^-$, $Br^-$, $I^-$, $HSO_4^-$, $NO_3^-$, $BF_4^-$, $ClO_4^-$, $IO_4^-$, $BH_4^-$ and $PF_6^-$ ions, as well as acetate and p-toluenesulfonate ions. The characteristics of the catalyst can also be influenced to a certain extend by the choice of the anion.

According to the invention, one proceeds preferably so that the solution of one or more quaternary ammonium compounds of the general formula (IO is admixed with the catalyst support; a solution containing the ions of the metal(s) belonging to Group A, and optionally those of the metal(s) belonging to Group B as well, is added to the mixture, and the reduction is performed. One can also proceed so that the compound(s) of the metal(s) belonging to Group A and optionally those of the metal(s) belonging to Group B are added to the solution of one or more compounds of the general formula (I), and then the support is added, and reduction is performed either directly in the resulting suspension or after separating the impregnated support from the liquid. In this instance, activated carbon, aluminum oxide, silicon dioxide or a molecular sieve is applied preferably as support.

According to a further process variant, the solution containing at least one compound of the general formula (I) is added to the solution containing the salt(s) of the metal(s) belonging to Group A and optionally those of the metal(s) belonging to Group B; thereafter the solution is admixed thoroughly with the support, the impregnated support is separated from the suspension, and finally reduced with hydrogen.

As mentioned above, the metal(s) are applied on the support in the presence of at least one compound of the general formula (I). In some instances, e.g., for the preparation of catalysts applicable for specific purposes, it is preferred to use a mixture of two or more compounds of the general formula (I).

Sometimes it is also preferred to apply compounds of the general formula (I) in which at least one of the substituents $R_1$, $R_2$, $R_3$ and $R_4$ is optically active. Catalysts prepared in the presence of such quaternary ammonium compounds can be applied particularly preferably to initiate or accelerate stereospecific reactions.

Reduction is performed preferably so that the solution containing at least one quaternary ammonium compound of the general formula (I), ions of at least one metal belonging to Group A and optionally ions of at least one metal belonging to Group B with the support suspended therein is treated with hydrogen at 0° to 150°

C. under a pressure of 0.01 to 100 atmospheres, or is reduced in the same temperature range with hydrazine hydrate, hydrazine mono- or dihydrochloride, formaldehyde, sodium borohydride or any other known reducing agent. It is generally preferred to perform the reduction with hydrogen at 25° C. under atmospheric pressure.

According to the invention, one can also proceed so that the solution containing at least one quaternary ammonium compound of the general formula (I) is admixed with a solution containing the ions of at least one metal belonging to Group A and optionally those of at least one metal belonging to Group B; the resulting solution is admixed with the support, thereafter the support is separated from the liquid, or the solvent is evaporated, and the impregnated support is reduced in a hydrogen stream at 100° to 300° C.

When a catalyst containing more than one catalytically active metal or a catalytically active metal and another metal inactive under certain conditions is to be prepared, one can proceed so that one of the metals is applied first onto the surface of the support as described above, and then the second metal is deposited onto the support already containing the first metal. However, the two metals can also be applied simultaneously onto the surface of the support.

The metals are applied primarily as their water-soluble salts in the method of the invention, of which the salts formed with mineral acids are particularly preferred. With some metals, however, oxides and salts formed with organic acids can be utilized as well. The catalysts are generally prepared with supports suspended in aqueous solutions; in some instances, however, it is preferred to apply organic solvents, primarily alcohols, as the reaction medium. With respect to the preparation process, one of the favorable properties of the quaternary ammonium compounds having the general formula (I) is that their aqueous solutions are also able to wet satisfactorily supports with highly hydrophobic surfaces (such as activated carbon). The use of the quaternary ammonium compounds involves the further advantage that they act as solubilizing agents for certain difficulty water-soluble or even water-insoluble compounds (such as amines, other nitrogen compounds and sulfur compounds) which can be applied to modify the properties of the catalysts according to known principles. Further, the quaternary ammonium compounds and/or decomposition products thereof remain in the catalysts of the invention, influencing the properties of these catalysts in a very desirable manner.

Of the major advantages of the method and catalysts according to the invention, the following are to be mentioned:

(a) The catalysts prepared according to the invention are much more active than those prepared by the known methods or available on the market. This increase in activity and efficiency (i.e., more end-product can be prepared per unit weight of metal) provides significant economical advantages primarily with catalysts of metals belonging to the platinum group.

(b) The catalysts can be prepared by a very simple process. No specific, time-consuming pre-treatment of the support is required. The process does not require any specific apparatus, and requires less time and manpower than the known ones.

(c) Catalysts for liquid phase and vapor phase reactions can equally be prepared by the process of the invention. The catalysts have a long life-span and retain their activity for a prolonged period. The catalysts prepared according to the invention can be applied in a large number of liquid phase reactions many more times than the commercially available ones.

(d) Both the catalytic effects and the other characteristics of the catalysts of industrial importance can be varied by the process of the invention over a wide range. By the proper combination of the metals, quaternary ammonium compounds, supports and the optional modifying agents, catalysts with optimum properties can be prepared for a given catalytic reaction.

The invention is elucidated in detail by the aid of the following non-limiting Examples.

EXAMPLE 1

Palladium/activated carbon catalyst

A 40% aqueous solution of 120 g of benzyl-trimethylammonium bromide is added to 1000 ml of distilled water. 90 g of activated carbon with a particle size below 100 um (specific surface area: 1150 $m^2/g$) are added to the resulting solution with continuous stirring. After 0.5 hour of stirring, an aqueous palladium chloride solution is introduced, and the resulting suspension is stirred for an additional 2 hours. (The aqueous palladium chloride solution is prepared by dissolving 16.69 g of palladium chloride in 20 ml of 36 w/w % aqueous hydrochloric acid and diluting the solution with water to 150 ml.) The suspension is poured into a hydrogenating flask mounted on a shaker, and the mixture is saturated with hydrogen at room temperature and atmospheric pressure. The flask is shaken at a rate of 200 r.p.m. After the termination of the hydrogen uptake (i.e., when 12 liters of hydrogen were consumed), the solid is filtered off on a sintered glass filter and washed several times with distilled water. The catalyst is dried in vacuo (20 mm Hg) at 50° C. The resulting catalyst contains 10% by weight of metallic palladium.

The extent of the dispersion of the catalytically active metal was determined by the carbon monoxide adsorption technique, widely applied in the testing of catalysts (see e.g. Brunelle, J. et al.: Journal of Catalysis 43, 273 (1976)). The dispersibility, calculated on the basis of the carbon monoxide adsorption measured at 20° C., is 0.51, i.e., more than the half of the palladium atoms are present on the surface. Consequently, the palladium is very finely distributed on the surface of the support. As a comparison, the dispersability of the commercially available 10 w/w% palladium catalysts varies between 0.08 and 0.15 according to the same test.

The catalysts proved to be very active in the liquid phase hydrogenation of several compounds. The following reactions are mentioned to demonstrate the activity of the catalyst:

Acetophenone was hydrogenated quantitatively to ethylbenzene in the presence of the catalyst (when a conventional catalyst is used, more 1-phenylethanol is produced than ethylbenzene).

Cinnamic aldehyde was hydrogenated to obtain propylbenzene as end-product (with a conventional catalyst, a mixture of cinnamic aldehyde, hydrocinnamic alcohol and cinnamic alcohol is obtained).

The catalyst proved to be particularly effective in the hydrogenation of 2-nitro-4-chloroaniline and β-naphthol. More than a hundredfold weight of 2-nitro-4-chloroaniline could be converted into o-phenylenediamine per unit weight of the catalyst, by utilizing the catalyst repeatedly in the reaction. (With the conventional catalysts, a weight ratio of 2 to 40 can be attained). β-Naphthol could be hydrogenated quantitatively into 5,6,7,8-tetrahydro-2-naphthol at 60° to 65° C. under a pressure of 4–5 atmospheres within 5–6 hours. The same reaction requires 24–32 hours with the conventional catalysts.

These results indicate that the catalyst has equally high activity in the hydrogenation of compounds with most diverse structures, and can be applied very advantageously in reactions which require the use of palladium catalysts.

EXAMPLE 2

Palladium/activated carbon catalyst

The palladium chloride solution prepared as described in Example 1 is added to 250 g of a 40 w/w % benzyl-tri-methylammonium chloride solution. After the dissolving of the precipitate initially formed, the solution is diluted to 1000 ml, and 90 g of finely ground activated carbon with a specific surface area of 1800 $m^2/g$ are added. The resulting suspension is stirred for 0.5 hour, and then the pH of the mixture is adjusted to between 9 and 11 with potassium hydroxide solution. Hydrogen is passed through the mixture at the rate of 1 to 15 liters/hour, and the suspension is stirred for a further 2 hours. Thereafter, the hydrogen steam is cut off, nitrogen is passed through the mixture, and the suspension is stirred for 15 minutes. The catalyst is filtered off, washed with distilled water and dried. The resulting catalyst contains 10% by weight of metallic palladium in a dispersion of 0.55.

This catalyst proved to be very active in the hydrogenation of 2-nitro-4-chloroaniline and -naphthol, as well as in the dehydrogenation of indoline to indole.

EXAMPLE 3

Palladium/aluminum oxide catalyst 100 g of tabletted aluminum oxide are admixed with a solution of 4 g of benzyl-trimethylammonium chloride in 200 ml of distilled water. A solution of 0.83 g of palladium chloride in 10 g of a 40 w/w % aqueous solution of benzyl-trimethylammonium chloride is added, and the resulting suspension is evaporated at 50° C. under a pressure of 20 mm Hg. The impregnated support is fed into a tube reactor provided with a heating jacket, a hydrogen stream is passed through the reactor, and the temperature is raised gradually to 200° C. within 2 hours. This temperature was maintained for one hour more in order to effect complete reduction. The resulting catalyst, which contains 0.5% by weight of palladium, proved to be very active in the hydrogenation of benzene to cyclohexane and phenol to cyclohexanone.

EXAMPLE 4

Palladium/silicon dioxide catalyst 100 g of tabletted silicon dioxide are admixed with a mixture of 20 ml of a 40 w/w % tetramethylammonium hydroxide solution and 180 ml of distilled water, and then 1.258 g of $Pd(NO_3)_2.2H_2O$, dissolved in 16 ml of a 40 w/w % aqueous tetramethylammonium hydroxide solution, are added. The resulting suspension is stirred for 2 hours, thereafter the impregnated support is filtered off and fed into the tube reactor described in Example 3. A hydrogen stream is passed through the reactor and the temperature of the catalyst bed is raised gradually to 250° C. within 3 hours. This temperature was maintained for one hour more in order to effect complete reduction. The resulting catalyst, which contains 0.5% by weight of palladium, proved to be very active in the hydrogenation of benzene to cyclohexane and o-nitro-ethylbenzene to o-ethylaniline.

EXAMPLE 5

Platinum/activated carbon catalyst 99 g of finely ground activated carbon are admixed with a solution of 30 g of benzyl-trimethylammonium chloride in 900 ml of distilled water. The suspension is stirred for 0.5 hour, and then a solution of 1.727 g of platinum tetrachloride in 50 ml of distilled water is added. After one hour of stirring, 1.6 g of hydrazine monochloride and then 12 g of sodium hydrocarbonate are added, and the suspension is poured into a hydrogenating flask mounted on a shaker. The flask is shaken at a rate of 250 r.p.m., and the suspension is saturated with hydrogen. After the termination of the hydrogen uptake, the catalyst is filtered off and dried. The resulting catalyst contains 1% by weight of platinum.

This catalyst proved to be very active in the liquid phase hydrogenation of 2-nitro-4-chloroaniline, β-naphthol and cinnamic aldehyde.

EXAMPLE 6

Rhodium/activated carbon catalyst 99 g of finely ground activated carbon are admixed with a solution of 12 g of benzyl-trimethylammonium chloride in 850 g of distilled water. After 0.5 hour of stirring, a solution of 2.085 g of rhodium chloride in 50 ml of distilled water is added. Thereafter, one proceeds as described in Example 1 to obtain a catalyst containing 1% by weight of rhodium.

This catalyst proved to be very active in the hydrogenation of cinnamic aldehyde and acetophenone.

EXAMPLE 7

Ruthenium/activated carbon catalyst 10.26 g of ruthenium chloride are dissolved in 50 ml of distilled water, and the solution is added to 120 g of a 40 w/w % benzyl-trimethylammonium chloride solution. After the dissolving of the precipitate initially formed, the solution is diluted to 1000 ml, and 95 g of finely ground activated carbon are introduced. Thereafter, one proceeds as described in Example 2 to obtain a catalyst containing 5% by weight of ruthenium.

This catalyst proved to be particularly active in the hydrogenation of β-naphthol and cinnamic aldehyde.

EXAMPLE 8

Iridium/activated carbon catalyst 0.27 g of $H_2IrCl_6.6H_2O$ is dissolved in 25 ml of distilled water, and the solution is added to 25 g of a 40 w/w % benzyl-trimethylammonium hydroxide solution. After the dissolving of the precipitate initially formed, the solution is diluted to 120 ml and 10 g of finely ground activated carbon are introduced. Thereafter, one proceeds as described in Example 2 to obtain a catalyst which contains 1% by weight of iridium.

This catalyst proved to be active in the hydrogenation of cinnamic aldehyde.

EXAMPLE 9

Silver/activated carbon catalyst 15.749 g of silver nitrate are dissolved in 150 g of a 40 w/w % tetrapropylammonium hydroxide solution. After the complete dissolving of the precipitate initially formed, the solution is diluted to 600 ml, and 90 g of activated carbon (particle size: 2–3 mm) are introduced. After one hour of stirring, 15 ml of hydrazine hydrate are added to the mixture, and stirring is continued for an additional 2 hours. Thereafter the catalyst is filtered off, washed with distilled water until neutral, and dried. The resulting catalyst contains 10% by weight of silver.

This catalyst proved to be very active and stable in the vapor phase dehydrogenation of cyclohexanol into cyclohexanone.

EXAMPLE 10

Gold/activated carbon catalyst 1.38 g of gold chloride are dissolved in 12 g of a 40 w/w % benzyl-trimethylammonium chloride solution. After the complete dissolving of the precipitate initially formed, the solution is diluted to 120 ml, and 9 g of finely ground activated carbon are introduced. Thereafter one proceeds as described in Example 2 to obtain a catalyst which contains 10% by weight of gold.

This catalyst proved to be active in the hydrogenation of cinnamic aldehyde at pressures above 25 atmospheres.

EXAMPLE 11

Cadmium/activated carbon catalyst 19.51 g of $CdCl_2.2H_2O$ are dissolved in 45 g of a 40 w/w % benzyl-trimethylammonium chloride solution, and the resulting solution was diluted to 120 ml. 90 g of activated carbon (particle size: 2–3 mm) are added, the suspension is stirred for one hour, and then a solution of 8 g of potassium hydroxide in 40 ml of distilled water is added. The resulting mixture is evaporated and the dry impregnated support is fed into a tube reactor. Hydrogen is passed through the reactor, and the temperature is increased gradually to 290° C. within 3 hours. The catalyst is maintained at the same temperature for 2 hours to obtain a catalyst with a cadmium content of 10% by weight.

This catalyst proved to be active and selective in the liquid phase hydrogenation of cinnamic aldehyde into cinnamic alcohol at 150° C. under a pressure above 50 atmospheres.

EXAMPLE 12

Palladium-copper/activated carbon catalyst 16.69 g of palladium chloride are dissolved in 20 ml of 36 w/w % hydrochloric acid, and the resulting solution is diluted to 120 ml. 250 g of a 40 w/w % benzyl-trimethylammonium chloride solution are added. The precipitate formed is allowed to dissolve; thereafter a solution of 2.62 g of $CuCl_2.2H_2O$ in 50 ml of distilled water is added, and the resulting solution is diluted to 1000 ml. 90 g of finely ground activated carbon are added to the solution, and then the mixture is treated as described in Example 2.

The resulting catalyst, containing 10% by weight of palladium and 1% by weight of copper, proved to be very active and selective in the hydrogenation of salicyclic chloride, 3,4,5-trimethoxybenzoyl chloride and p-acetoxybenzoyl chloride. In these reactions, the respective aldehyde was obtained with a selectivity above 90%, and, depending on the purity of the starting acid chloride, the catalyst could be applied 5–15 times for the hydrogenation of a tenfold amount of the acid chloride.

EXAMPLE 13

Osmium/activated carbon catalyst 0.231 g of $(NH_4)_2OsCl_6$ is dissolved in 30 g of a 40 w/w % benzyl-trimethylammonium hydroxide solution, and the resulting solution is diluted to 50 ml. 9.9 g of finely ground activated carbon are added to the solution. Thereafter, one proceeds as described in Example 1 to obtain a catalyst with an osmium content of 1% by weight.

This catalyst proved to be active in the hydrogenation of cinnamic aldehyde.

EXAMPLE 14

Platinum-palladium/activated carbon catalyst 98 g of finely ground activated carbon are admixed with a solution of 45 g of benzyl-trimethylammonium chloride in 1000 ml of distilled water. After 0.5 hour of stirring, 1.669 g of palladium chloride, dissolved in a mixture of 5 ml of 36 w/w % hydrochloric acid and 50 ml of distilled water, and then 1.727 g of platinum tetrachloride, dissolved in 50 ml of distilled water, are added. Thereafter, one proceeds as described in Example 5 to obtain a catalyst containing 1% by weight of platinum and 1% by weight of palladium.

This catalyst proved to be very active in the liquid phase hydrogenation of cinnamic aldehyde, -naphthol, o-nitrophenylethanol and 1-hexene-5-one.

EXAMPLE 15

Palladium-ruthenium/activated carbon catalyst 16.69 g of palladium chloride are dissolved in 20 ml of 36 w/w % hydrochloric acid, and the resulting solution is diluted to 80 ml. 10.25 g of ruthenium chloride are dissolved in 60 ml of distilled water. These solutions are added to 280 g of a 40 w/w % benzyl-trimethylammonium chloride solution, and the resulting mixture is diluted to 1000 ml. 85 g of finely ground activated carbon are added to the solution. Thereafter, one proceeds as described in Example 2 to obtain a catalyst containing 10% by weight of palladium and 5% by weight of ruthenium.

This catalyst proved to be very active in the liquid phase hydrogenation of cinnamic aldehyde, acetophenone, o-nitroethylbenzene, o-nitrophenyl-ethanol, β-naphthol, 1-hexen-5-one and itaconic acid dimethyl ester.

EXAMPLE 16

Palladium-rhodium/activated carbon catalyst 98 g of finely ground activated carbon are admixed with a solution of 25 g of benzyl-trimethylammonium chloride in 900 ml of distilled water. After 0.5 hour of stirring, a solution of 1.669 g of palladium chloride in 36 w/w % hydrochloric acid, diluted to 50 ml, is added. Thereafter, the palladium is reduced as described in Example 2. When the reduction terminates, a solution of 2.085 g of rhodium chloride in 50 ml of distilled water is added to the suspension, and the mixture is reduced again as described in Example 2. The resulting catalyst contains 1% by weight of palladium and 1% by weight of rhodium.

This catalyst is very active in the liquid phase hydrogenation of cinnamic aldehyde, 2-nitro-4-chloroaniline, o-nitrophenyl-ethanol and itaconic acid dimethyl ester.

EXAMPLE 17

Palladium-silver/activated carbon catalyst 2.516 g of $Pd(NO_3)_2.2H_2O$ and 0.787 g of silver nitrate are dissolved in 50 ml of a 40 w/w % solution of tetraethylammonium hydroxide, and the resulting solution is diluted to 100 ml. 8.5 g of finely ground activated carbon are added to this solution. Thereafter, one proceeds as described in Example 1 to obtain a catalyst containing 10% by weight of palladium and 3% by weight of silver.

This catalyst proved to be active and selective in the liquid phase hydrogenation of the following acid chlorides: salicylic chloride, p-acetoxybenzoyl chloride and 3,4,5-trimethoxy-benzoyl chloride.

EXAMPLE 18

Palladium-gold/activated carbon catalyst 8.5 g of finely ground activated carbon are admixed with 50 g of 40 w/w % benzyl-trimethylammonium chloride dissolved in 100 ml of distilled water. After 0.5 hour of stirring, a solution of 1.669 g of palladium chloride in 36 w/w % hydrochloric acid, diluted to 50 ml, and then a solution of 0.77 g of gold chloride in 50 ml of distilled water are added. Thereafter, one proceeds as described in Example 2 to obtain a catalyst containing 10% by weight of palladium and 5% by weight of gold.

This catalyst proved to be active and selective in the selective hydrogenation of salicylic chloride and 3,4,5-trimethoxybenzoyl chloride.

EXAMPLE 19

Palladium-cadmium/activated carbon catalyst 8.5 of finely ground activated carbon are admixed with 25 g of 40 w/w % benzyl-trimethylammonium chloride dissolved in 100 ml of distilled water. After 0.5 hour of stirring, a solution of 1.669 g of palladium chloride in 36 w/w % hydrochloric acid, diluted to 50 ml, and then a solution of 0.985 g of $CdCl_2.2H_2O$ in 50 ml of distilled water are added. Thereafter, one proceeds as described in Example 2 to obtain a catalyst containing 10% by weight of palladium and 5% by weight of cadmium.

This catalyst proved to be active and selective in the liquid phase hydrogenation of salicyclic chloride, 3,4,5-trimethoxybenzoyl chloride and 4-chlorobutyryl chloride.

EXAMPLE 20

Palladium/activated carbon catalyst 12 g of (+)-1-phenylethyl-trimethylammonium iodide are dissolved in 250 g of a 40 w/w % aqueous solution of benzyl-trimethylammonium chloride. The resulting solution is diluted to 1000 ml, and 90 g of finely ground activated carbon are added. After 0.5 hour of stirring, 16.69 g of palladium chloride dissolved in 20 g of 36 w/w % hydrochloric acid, diluted to 100 ml, is added. Thereafter, one proceeds as described in Example 2 to obtain a catalyst containing 10% by weight of palladium.

This catalyst proved to be active in the hydrogenation of cinnamic aldehyde. This catalyst can also be applied in stereoselective or enantioselective hydrogenation processes: thus, in the stereoselective liquid phase hydrogenation of 6-dimethyl-6-deoxy-6-methylene-5-oxy-tetracycline and phenyl-pyridylacetic acid ethyl ester.

EXAMPLE 21

Palladium-zinc/activated metal catalyst 80 ml of a 40 w/w % aqueous benzyl-trimethylammonium chloride solution are added to 900 ml of distilled water, and 94 g of finely ground activated carbon are added to the resulting solution under continuous stirring. After 0.5 hour of stirring, a metal chloride solution (prepared by dissolving 8.35 g of palladium chloride in 10 ml of 36 w/w % hydrochloric acid, diluting the solution to 100 ml and admixing it with 2.085 g of zinc chloride dissolved in 20 ml of distilled water) is added to the suspension. Thereafter, one proceeds as described in Example 2 to obtain a catalyst containing 5% by weight of palladium and 1% by weight of zinc.

This catalyst proved to be very active and selective in the hydrogenation of 1-hexene-5-one and acyl chlorides, and can be used to advantage, e.g., in the preparation of 4-chlorobutyraldehyde, salicylaldehyde and 3,4,5-trimethoxybenzaldehyde by selectively hydrogenating the respective acyl chlorides.

EXAMPLE 22

Palladium-mercury/activated carbon catalyst

This catalyst is prepared as described in Example 21 with the difference that 1.35 g of mercury chloride dissolved in 40 ml of distilled water are added to the palladium chloride solution instead of zinc chloride. The resulting catalyst contains 5% by weight of palladium and 1% by weight of mercury. This catalyst is particularly active and selective in the hydrogenation of acyl chlorides into the corresponding aldehydes.

EXAMPLE 23

Palladium-germanium/activated carbon catalyst 1.669 g of palladium chloride are dissolved in 3 ml of 36 w/w % hydrochloric acid. The excess of hydrochloric acid is removed by evaporation, and 25 ml of a 40 w/w % tetrapropylammonium hydroxide solution are added to the residue. Palladium chloride is dissolved in this solution by gentle heating. 1.44 g of germanium oxide are dissolved separately in 20 ml of a 40 w/w % tetrapropylammonium hydroxide solution. Thereafter the two solutions are combined and diluted to 250 ml with distilled water. 8 g of finely ground activated carbon are added to the resulting solution. The suspension is heated to 80° C. under continuous stirring, and at this temperature hydrogen is passed through the suspension for 6 hours. Thereafter the hydrogen stream is cut off, nitrogen is passed through the suspension and the suspension is gradually allowed to cool to room temperature. The reduced catalyst is filtered off, washed with distilled water, and dried. The resulting catalyst contains 10% by weight of palladium and 9.6% by weight of germanium.

This catalyst was particularly active in the hydrogenation of nitro compounds; thus, e.g., in the hydrogenation of nitrobenzene, 2-nitro-4-chloroaniline and 2,6-dinitro-toluene to the respective amines, as well as in the hydrogenation of nitric acid to hydroxylamine.

EXAMPLE 24

Palladium-tin/activated carbon catalyst

A solution of palladium chloride in tetrapropylammonium hydroxide solution is prepared as described in Example 23. 1.597 g of tin chloride are dissolved separately in 15 ml of a 40 w/w % tetramethylammonium hydroxide solution under gentle heating. The two solutions are combined. Thereafter, one proceeds as described in Example 23 to obtain a catalyst containing 10% by weight of palladium and 9.7% by weight of tin.

This catalyst proved to be selective in the liquid phase hydrogenation of cinnamic aldehyde and 1-hexene-5-one.

EXAMPLE 25

Palladium-antimony/activated carbon catalyst

One proceeds as described in Example 24 with the difference that 1.87 g of antimony trichloride are dissolved in 20 ml of a 40 w/w % tetramethylammonium hydroxide solution instead of tin chloride. A catalyst containing 10% by weight of palladium and 9.8% by weight of antimony is obtained.

This catalyst was selective in the liquid phase hydrogenation of cinnamic aldehyde.

EXAMPLE 26

Palladium-lead/activated carbon catalyst 30 ml of a 40 w/w % benzyl-trimethylammonium chloride solution are diluted with 100 ml of distilled water, and 8 g of finely ground activated carbon are added to the solution. After 0.5 hour of stirring, a metal salt solution, prepared by dissolving 1.669 g of palladium chloride in 3 ml of 36 w/w % hydrochloric acid, diluting the solution to 80 ml and admixing it with 1.60 g of lead nitrate, is added to the suspension. Thereafter one proceeds as described in Example 2 to obtain a catalyst containing 10% by weight of palladium and 8.5% by weight of lead.

This catalyst was active and selective in the hydrogenation of 2-methyl-3-butyn-2-ole.

EXAMPLE 27

Platinum-zinc/activated carbon catalyst 35 ml of a 40 w/w % benzyl-trimethylammonium chloride solution are added to 800 ml of distilled water, 98.5 g of finely ground activated carbon are added to this solution, the resulting suspension is stirred for 0.5 hour and then 1.727 g of platinum tetrachloride and 1.04 g of zinc chloride dissolved in 50 ml of distilled water are added. Thereafter, one proceeds as described in Example 5 to obtain a catalyst containing 1% by weight of platinum and 0.5% by weight of zinc.

This catalyst proved to be particularly selective in the liquid phase hydrogenation of acyl chlorides, such as 4-chlorobutyryl chloride, salicylic chloride and 3,4,5-trimethoxybenzoyl chloride.

What we claim is:

1. A process for the preparation of a supported metal catalyst containing at least one metal belonging to Group A and optionally at least one metal belonging to Group B, wherein Group A metals are selected from the group consisting of palladium, rhodium, ruthenium, platinum, iridium, osmium, silver, gold and cadmium and Group B metals are selected from the group consisting of zinc, mercury, germanium, tin, antimony and lead, by reductive deposition of the metal(s) onto the support with a solution containing the ions or compounds of the metal(s) in question and then reducing the support, characterized in that the metal(s) is (are) applied onto the support in the presence of at least one compound of the general formula (I),

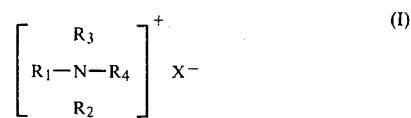

wherein
$R_1$, $R_2$, $R_3$ and $R_4$ each stands for a straight-chained or branched $C_{1-20}$ alkyl group, a $C_{1-4}$ hydroxyalkyl group or a phenyl-($C_{1-4}$ alkyl) group optionally having additional substituents, preferably $C_{1-4}$ alkyl groups, on the phenyl ring, and X is hydroxy group or the residue of an organic or mineral acid, that the reduction is effected by hydrogenation at a temperature not exceeding 300° C., and that no calcining step is used.

2. A process as claimed in claim 1, characterized in that a solution of at least one compound of the general formula (I) is admixed with the support, a solution containing the ions of the metal(s) belonging to Group A and optionally those of the metals belonging to Group B, too, is added to the mixture, and the resulting substance is hydrogen reduced.

3. A process as claimed in claim 1, characterized in that the compound(s) of the metal(s) belonging to Group A and optionally those of the metal(s) belonging to Group B are added to the solution of at least one compound of the general formula (I), then the support, selected from the group consisting of activated carbon, aluminum oxide, silicon dioxide or a molecular sieve, is added, and hydrogen reduction is performed either directly in the resulting suspension or after separating the support from the liquid.

4. A process as claimed in claim 1, characterized in that a solution of at least one compound of the general formula (I) is added to the solution containing the salt(s) of the metal(s) belonging to Group A and optionally those of the metal(s) belonging to Group B, the solution is admixed with the support, the support is separated from the suspension and reduced with hydrogen.

5. A process as claimed in any of claims 1 to 4, characterized in that a compound of the general formula (I) in which at least one of substituents $R_1$, $R_2$, $R_3$ and $R_4$ is optically active is applied.

6. A process as claimed in claim 1, characterized in that the compound(s) of general formula (I) and the compound(s) of the metal(s) belonging to Group A are used in a molar ratio of from 1.1/1 to 132.1/1.

7. A process for the preparation of a supported metal catalyst containing at least one metal belonging to Group A and optionally at least one metal belonging to Group B, wherein Group A metals are selected from the group consisting of palladium, rhodium, ruthenium, platinum, iridium, osmium, silver, gold and cadmium and Group B metals are selected from the group consisting of zinc, mercury, germanium, tin, antimony and lead, by reductive deposition of the metal(s) onto the support by impregnating the support with a solution containing the ions or compounds of the metal(s) in question to form a suspension and then reducing the suspension, characterized in that the metal(s) is (are) applied onto the support in the presence of at least one compound of the general formula (I),

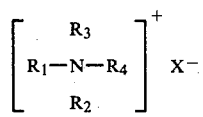 (I)

wherein
R$_1$, R$_2$, R$_3$ and R$_4$ each stands for a straight-chained or branched C$_{1-20}$ alkyl group, a C$_{1-4}$ hydroxyalkyl group or a phenyl-(C$_{1-4}$ alkyl) group optionally having additional substituents, preferably C$_{1-4}$ alkyl groups, on the phenyl ring, and X is hydroxy group or the residue of an organic or mineral acid, that the reduction is effected by hydrogenation at a temperature not exceeding 300° C., and that no calcining step is used.

8. The process of claim 7 wherein said suspension is treated with hydrogen at 0° to 150° C., at a pressure of 0.01 to 100 atmospheres.

9. The process of claim 7 wherein said hydrogenation is effected at 25° C. under atmospheric pressure.

10. A process for the preparation of a supported metal catalyst containing at least one metal belonging to Group A and optionally at least one metal belonging to Group B, wherein Group A metals are selected from the group consisting of palladium, rhodium, ruthenium, platinum, iridium, osmium, silver, gold and cadmium and Group B metals are selected from the group consisting of zinc, mercury, germanium, tin, antimony and lead, by reductive deposition of the metal(s) onto the support by impregnating the support with a solution containing the ions or compounds of the metal(s) in question to form a suspension and then reducing the suspension, characterized in that the metal(s) is (are) applied onto the support in the presence of at least one compound of the general formula (I),

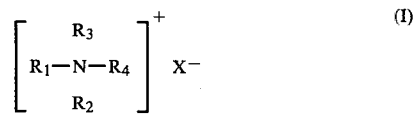 (I)

wherein
R$_1$, R$_2$, R$_3$ and R$_4$ each stands for a straight-chained or branched C$_{1-20}$ alkyl group, A C$_{1-4}$ hydroxyalkyl group or a phenyl-(C$_{1-4}$ alkyl) group optionally having additional substituents, preferably C$_{1-4}$ alkyl groups, on the phenyl ring, and X is hydroxy group or the residue of an organic or mineral acid, that the reduction is effected by hydrogenation at a temperature not exceeding 300° C., that no calcining step is used, and that the compound(s) of general formula (I) and the compound(s) of the metal(s) belonging to Group A are used in a molar ratio of 1.1/1 to 132.1/1.

* * * * *